United States Patent
Legay

(10) Patent No.: US 9,101,781 B2
(45) Date of Patent: Aug. 11, 2015

(54) IMPLANTABLE CARDIAC PROSTHESIS GENERATOR HAVING PROTECTION FROM AN MRI EXAMINATION

(71) Applicant: SORIN CRM S.A.S., Clamart Cedex (FR)

(72) Inventor: Thierry Legay, Fontenay les Briis (FR)

(73) Assignee: SORIN CRM S.A.S., Clamart Cedex (FR)

( * ) Notice: Subject to any disclaimer, the term of this patent is extended or adjusted under 35 U.S.C. 154(b) by 16 days.

(21) Appl. No.: 14/065,145

(22) Filed: Oct. 28, 2013

(65) Prior Publication Data

US 2014/0052200 A1    Feb. 20, 2014

Related U.S. Application Data

(63) Continuation of application No. 12/643,846, filed on Dec. 21, 2009, now Pat. No. 8,583,255.

(30) Foreign Application Priority Data

Dec. 19, 2008   (FR) ..................................... 08 07148

(51) Int. Cl.
| A61N 1/00 | (2006.01) |
| A61N 1/39 | (2006.01) |
| A61N 1/37 | (2006.01) |
| A61N 1/08 | (2006.01) |

(52) U.S. Cl.
CPC ................ *A61N 1/3962* (2013.01); *A61N 1/37* (2013.01); *A61N 1/3718* (2013.01); *A61N 1/3931* (2013.01); *A61N 2001/086* (2013.01)

(58) Field of Classification Search
CPC ........................................................ A61N 1/08
USPC .......................................................... 607/4, 63
See application file for complete search history.

(56) References Cited

U.S. PATENT DOCUMENTS

| 2007/0088416 | A1 | 4/2007 | Atalar et al. |
| 2007/0255332 | A1 | 11/2007 | Cabelka et al. |
| 2008/0221638 | A1 | 9/2008 | Wedan et al. |

FOREIGN PATENT DOCUMENTS

| EP | 1 632 265 | 3/2006 |
| WO | WO-03/063946 | 8/2003 |
| WO | WO-2008/036865 | 3/2008 |

OTHER PUBLICATIONS

Preliminary Search Report for French Patent Application No. 0807148, dated Jun. 30, 2009, 2 pages.

*Primary Examiner* — Christopher D Koharski
*Assistant Examiner* — Nadia A Mahmood
(74) *Attorney, Agent, or Firm* — Foley & Lardner LLP

(57) ABSTRACT

Systems, methods, and devices for protecting against effects of magnetic fields are provided. One implantable medical device includes a lead including a first conductor and a second conductor. The device further includes a generator including an electronic circuit, a metal housing that has a ground potential, and one or more switching devices. The switching devices, in a safekeeping configuration, are configured to disconnect the second conductor from the electronic circuit and to connect the second conductor to the ground potential of the metal housing. The first conductor is connected to the electronic circuit in the safekeeping configuration. The switching devices, in the safekeeping configuration, are configured to cause the second conductor to shield the first conductor from at least a portion of the effects of the magnetic field while the first conductor remains connected to the electronic circuit for use in performing a sensing operation and/or a stimulation operation.

19 Claims, 1 Drawing Sheet

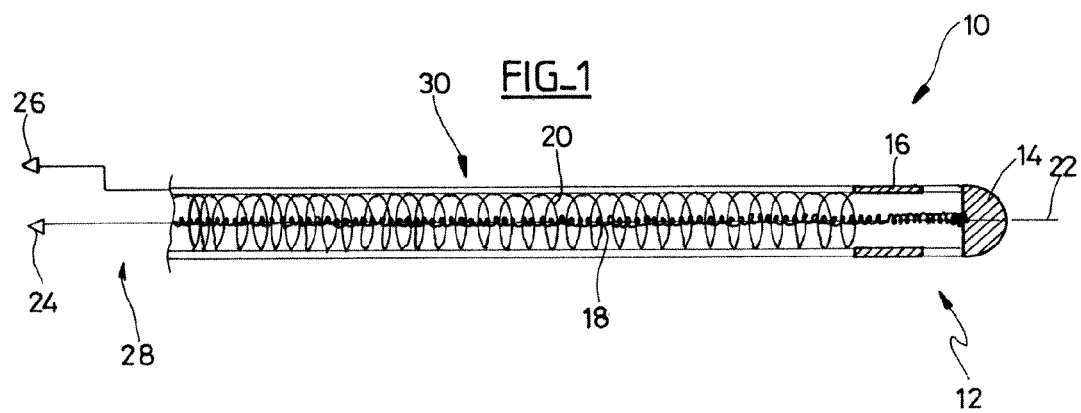
FIG_1
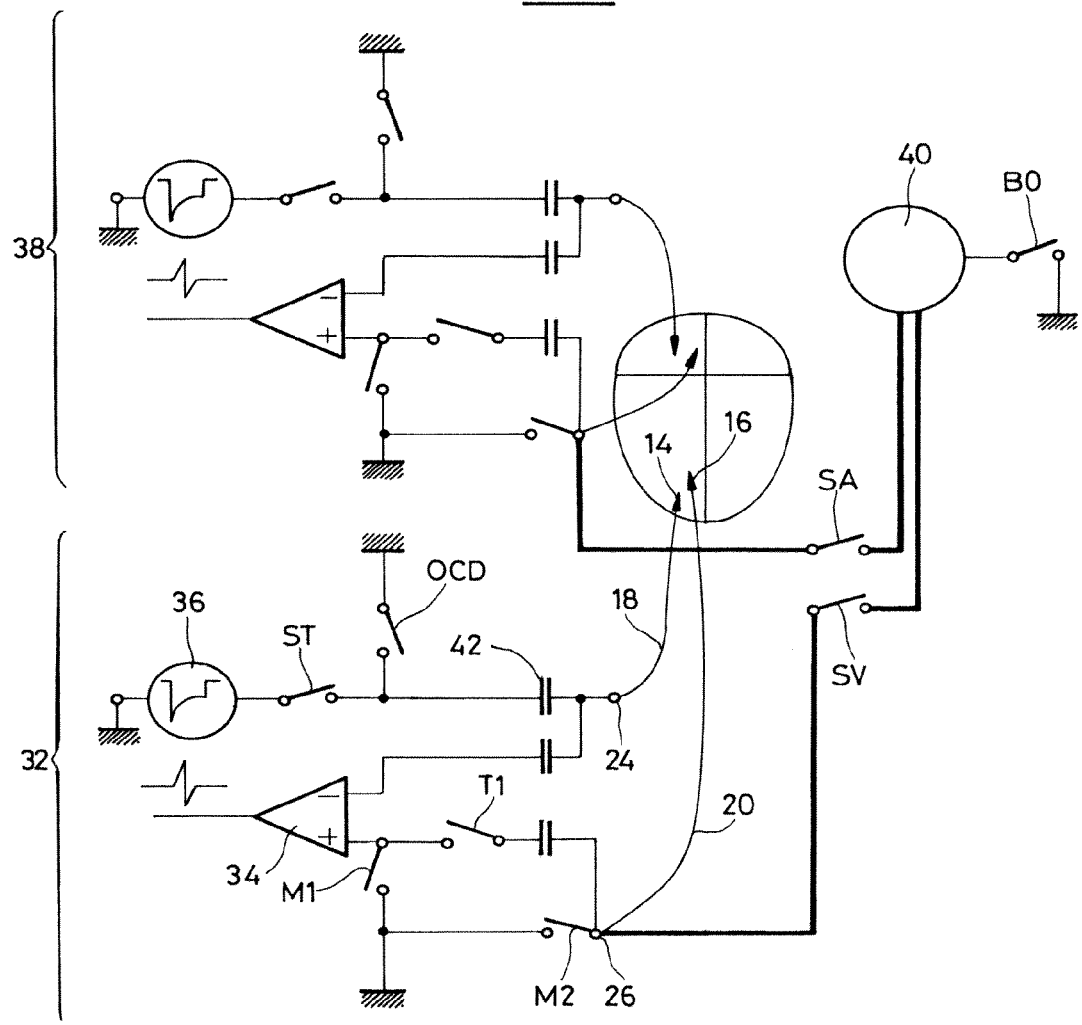
FIG_2

IMPLANTABLE CARDIAC PROSTHESIS GENERATOR HAVING PROTECTION FROM AN MRI EXAMINATION

CROSS-REFERENCE TO RELATED APPLICATION

This application is a continuation of U.S. patent application Ser. No. 12/643,846, filed Dec. 21, 2009, which claims the benefit of and priority to French Patent Application No. 0807148, filed Dec. 19, 2008. Both U.S. patent application No. 12/643,846 and French Patent Application No. 0807148 are hereby incorporated by reference in their entireties.

BACKGROUND

The present invention relates to "active implantable medical devices" as defined by the 20 Jun. 1990 Directive 90/385/EEC of the Council of European Communities, more specifically to devices that continuously monitor a patient's heart rhythm and deliver to the heart, if necessary, a resynchronization and/or a defibrillation electrical stimulation pulse, in response to an appropriate arrhythmia detected by the device. The present invention relates more particularly to techniques for safekeeping (i.e., protecting) these implantable devices (having generators and their associated sensors) when the patient is subjected to examination by magnetic resonance imaging (MRI).

The active implantable devices associated with the present invention typically include a housing, generally designated as a "generator", that is electrically and mechanically connected to one or more leads. The leads are equipped with electrodes that are intended to come into contact with the patient's myocardium at those sites where the electrical potentials are detected (collected) and/or the stimulation pulses are delivered (applied). These electrodes can be endocardial electrodes (e.g., electrodes that are placed in a cavity of the myocardium in contact with the wall of the myocardium), epicardial electrodes (e.g., electrodes that are preferably used to define a reference potential, or to apply a shock stimulation pulse), or intravascular electrodes (e.g., electrodes that are introduced into the coronary sinus and advanced to a position that faces the myocardial wall of the left ventricle).

Heretofore, an MRI examination was contraindicated for patients having an implanted cardiac pacemaker or defibrillator. This is for several reasons, including, for example:
- heating near the electrodes connecting the generator to the patient's heart;
- forces and torques of attraction exerted on the device immersed in high intensity magnetic fields generated by an MRI equipment; and
- unpredictable behavior of the device itself, due to exposure to extreme magnetic fields.

The problem of heating exists especially in the vicinity of leads equipped with electrodes that are connected to the generator. Indeed leads that are placed in an MRI imaging equipment behave like antennas and couple (collect) the radiofrequency (RF) energy emitted by the MRI imager. The frequency of the RF field is equal to the Larmor frequency of protons, $f=42.56 \times B0$, in Tesla, the characteristic static induction of the MRI imager. For typical static inductions B0 of 1.5 T and 3 T, the RF frequencies correlatively generated by the MRI imager are approximately 64 MHz and 128 MHz respectively.

Indeed, the heating at the electrodes is proportional to the density of current flowing through them. Hence, the smaller the surface of the electrode, the higher the current density and the greater the heating of the surrounding tissues.

In practice, depending on the configuration of the generator, the leads, and the MRI imaging equipment, the temperature rise typically varies from 8° C. (for carbon electrodes) to 12° C. (for metal electrodes), and sometimes even up to 30° C.

The elevated temperature should not exceed 2° C. as specified in the EN 45502-1 standard and its derivatives. At a temperature increase of 4° C. or more, cell death can occur locally. This has as an immediate effect, among others, to irreversibly alter the characteristics of detection and stimulation of cardiac activity.

It is possible, as described in the U.S. Published Application 2007/0255332 A1, to provide a method for safekeeping a device from MRI in which any stimulus is inhibited, and a protection circuit at the connector housing to isolate the conductors of the generator circuits, and to connect all these conductors to the ground of the generator housing to prevent induced parasitic currents. But this procedure prevents the device from functioning for the duration of an MRI examination. An MRI examination can last several minutes, thus it is highly desirable that the device continues during the MRI examination period to provide seamless operation for detecting potential depolarizations at, and delivering stimulation pulses to, the myocardium. To achieve this, during the MRI examination, the device is switched to a protected mode of operation and disables circuits that are sensitive to high magnetic fields, such as RF telemetry circuits, and switching power supplies.

It is thus not sufficient, in practice, to simply disconnect all conductors of the lead and/or to connect them to ground for the duration of an MRI examination, in order to avoid induction of current flow.

To reduce the induced current flow in the lead conductors, it has been proposed to put a filter opposing the current flow in series with the conductors in the path of the induced currents. The filter may be a simple inductor, however, the attenuation of the induced currents is usually not sufficient. It also has been proposed to insert in the current loop an L-C type resonant circuit, tuned to the RF frequency generated by an MRI imager. But this solution has a drawback of requiring different types of filters depending on the RF characteristic frequencies of the MRI imager (e.g., 64 MHz, 128 MHz) because the RF characteristic frequencies vary from one device to another, as explained above.

SUMMARY

It is, therefore, an object of the present invention to solve the problem of heating near the electrodes connecting the generator to the patient's heart as might occur during an MRI examination.

The starting point of the present invention is the discovery by the inventors that one can seek protection of another nature: instead of limiting the current flow in the lead conductors, the present invention avoids, or at least reduces, the exposure of these conductors to RF induced magnetic fields generated by an MRI imager, by implementing a shielding technique that prevents or minimizes induction of RF currents in the conductors.

The use of shielded conductors in place of conductors of an implanted device would certainly be possible. However, it would require a new design of leads, and in any event would not apply to already implanted leads.

According to one embodiment, the present invention advantageously connects to leads of a bipolar type having at least two conductors: one connected to the distal electrode having a small surface in direct contact with the myocardium, the other connected to the most extended proximal electrode, which remains floating in the heart. This embodiment is further directed towards implementing during an MRI examination a particular configuration of sensing and stimulation of the myocardium, in which only the conductor connected to the distal electrode is functionally used for detection (or sensing)/stimulation, and the other conductor is maintained at the same potential as the metal housing of the generator that is electrically grounded to the device. In this configuration, one lead remains functional as a unipolar lead for the detection and stimulation operations, and the other conductor is temporarily used as a shielding conductor during the MRI examination.

One aspect of the invention is directed to a generator for an active implantable medical device of the cardiac stimulation, resynchronization and/or defibrillation prosthetic type of the generic type disclosed by U.S. 2007/0255332 A1 cited above. Such a device comprises a generator coupled to a detection/stimulation lead wherein:

the lead comprises: at least two distal electrodes at a proximal connector; and at least two conductors extending along the length of the lead from its distal end to its proximal end to connect the electrodes to respective terminals of the lead connector.

the generator comprises: a metal housing; an electronic detection/stimulation circuit integrated in the housing; a connector comprising connection terminals connected to the electronic circuit of detection/stimulation and capable of being coupled to respective terminals of the connector of the lead; and means for MRI safekeeping, able to place the circuit of the generator in a configuration that is protected against the deleterious effects of exposure of the lead to magnetic fields that may be encountered during an MRI Examination by magnetic resonance.

To that purpose, the means for MRI safekeeping of the generator characteristically includes a means to temporarily connect one of the terminals of the connector to the potential of the metal housing, and the other remaining terminal or terminals connected to the electronic detection/stimulation circuit.

In a preferred embodiment, the lead is of a coaxial type with an internal conductor connected to an axial distal electrode, and an external conductor connected to a proximal electrode. In this embodiment, the means for MRI safekeeping includes a means for temporarily setting to the potential of the metal housing the connection terminal that is coupled to the external conductor of the lead, and keeping connected to the electronic detection/stimulation circuit the terminal link that is coupled to the internal conductor of the lead.

In another embodiment, the lead is of a co-radial type comprising two separate external conductors connected to two respective electrodes. In this embodiment, the means for MRI safekeeping includes a means for temporarily setting to the potential of the metal housing the connection terminal that is coupled to one of the external conductors of the lead, and keeping connected to the electronic detection/stimulation circuit the terminal connection that is coupled to the other external conductor of the lead.

Another aspect of the present invention is directed to a method of protecting an active implantable medical device as above, this method comprising a step of safekeeping by temporarily connecting one of the generator connector terminals to the potential of the metal housing, and leaving the other terminal link or terminal links connected to the electronic detection/stimulation circuit.

The method advantageously comprises a detection of a magnetic field by the generator, with the safekeeping step being performed on detection of the magnetic field, preferably only on detection of the magnetic field, and more preferably only during the existence of the magnetic field. The method may provide for mandatory suspension of safekeeping after expiry of a predetermined period of time.

BRIEF DESCRIPTION OF THE FIGURES

Further features, characteristics, and advantages of the present invention will become apparent to a person of ordinary skill in the art from the following detailed description and preferred embodiments of the present invention, made with reference to the annexed drawings, in which like reference characters refer to like elements, and in which:

FIG. 1 is a sectional view of a coaxial lead implementing a first embodiment of the present invention; and FIG. 2 is an exemplary diagram of a switching circuit of a generator, in accordance with an implementation of the present invention.

DETAILED DESCRIPTION

As regards its software aspects, the invention can be implemented by an appropriate programming of the controlling software of a known pacemaker, for example of the cardiac pacemaker, resynchronizer and/or defibrillator type, including circuits for the acquisition of a signal provided by endocardial leads and/or one or more implanted sensors. The adaptation of the known devices to implement the functions of the present invention is believed to be within the abilities of a person of ordinary skill in the art, and therefore will not be described in detail.

The invention may particularly be applied to implantable devices such as those of the Reply and Paradym families produced and marketed by Sorin CRM (formerly known as ELA Medical), Montrouge, France. These devices include programmable microprocessor circuitry to receive, format, and process electrical signals collected by electrodes implanted and deliver low energy pacing pulses to these electrodes. It is possible to transmit from a programmer to the device by telemetry software that will be stored in a memory of the device and executed to implement the functions of the present invention that will be described below, with reference to the drawings.

FIG. 1 illustrates an example of a lead 10 of the coaxial type. At its distal end 12, the lead 10 has two electrodes including a distal electrode or "tip" 14 having a small surface (e.g., a few $mm^2$), and an annular proximal electrode or "ring" 16 having a larger surface (e.g., tens of $mm^2$). The distal electrode 14 is intended to come into direct contact with the myocardial tissue in an atrial or a ventricular cavity. The proximal electrode 16 is intended to be floating inside the heart chamber, interfacing with blood.

The distal electrode 14 is connected to an inner conductor 18 while the proximal electrode 16 is connected to an external conductor 20 wound on the periphery of the body of the lead 10. These conductors 18 and 20 are isolated from each other and from the external environment by means of internal and external insulating sheaths, not shown. The inner conductor 18 is preferably a coiled conductor extending axially along the main axis 22 of the lead 10, so as to leave open in the central part a space sufficient to form a central lumen in which, for example, a wire guide may be introduced during implantation. The conductors 18 and 20 lead to respective terminals 24 and 26 at the proximal end 28 of the lead 10, these terminals being part of a connector (not shown) for mechanically and electrically coupling the lead 10 to a generator of the implanted device.

Essentially, the invention proposes to connect the external conductor 20 to the ground and keep it connected to the electric potential of the metal housing of the generator so that the conductor 20 acts as a shield for the internal conductor 18 along the length of the central part 30 of the lead 10. This shield provides a protection similar to that obtained by a coaxial cable used for conducting electrical signals of low voltage.

In an alternative embodiment, the present invention applies to leads of a "co-radial" type, in which both conductors have their own isolation, and are spiralled side by side around the main axis 22 of the lead 10. In this case, the shielding effect is obtained by the proximity of one conductor that is connected to the ground, relative to the other functional conductor that is ungrounded and connected to the distal electrode.

In either embodiment (coaxial or co-radial lead), even if the two conductors are arranged differently, they are always geometrically kept close to each other. In this respect, the one conductor that remains functionally connected to the distal electrode is protected by the other conductor connected to ground, and is used to detect cardiac spontaneous waves and deliver stimulation pulses. The shielding by the proximal conductor that is temporarily connected to the ground limits the antenna phenomenon of the lead when placed in an RF field of the MRI imager, therefore limiting induced current in the distal conductor to remain functional.

FIG. 2 shows a preferred embodiment of a switching circuit of the generator in accordance with the present invention.

It is noted that there is no need to modify the lead to implement the invention, because the switching is performed by the generator. This has the advantage, firstly, that no redesign of the lead is necessary and, secondly, that the invention can be applied to existing leads, already implanted, simply by a change of generator. The change of generator at its end of life is generally performed without a change of the lead.

The generator has a stage 32 with a ventricular sensing amplifier 34 and a ventricular pulse generator circuit of ventricular pacing 36. According to one embodiment, the generator includes a similar atrial stage 38, which is illustrated but not described in detail, insofar as the various switches are operated in the same way to result in the same configurations described below.

The detection/stimulation circuits 34 and 36 are connected to the distal electrode 14 and the proximal electrode 16 via respective conductors 18 and 20 that are connected to corresponding terminals 24 and 26.

The terminals 24 and 26 are coupled to circuits 34 and 36 by the various switches M1, M2, T1, and ST. An OCD switch allows the discharge of a connection capacitor 42 after delivering a stimulation pulse (an aspect of a generic implanted medical device, thus not described in detail). A switch B0 is provided to selectively connect the metal housing 40 of the generator to the electrical ground of the different electrical circuits integrated inside said metal housing 40.

For a bipolar sensing configuration, the switches are configured as follows: B0 closed, M1 and M2 open, T1 closed, and ST open.

For a unipolar sensing configuration, the switches are configured as follows: B0 closed, M1 closed, and M2, T1 and ST open.

For a bipolar stimulation configuration, stimulation pulses are delivered between the distal and proximal electrodes. The proximal electrode is connected to the ground and the electrical voltage of the housing 40 is floating. The switches are configured as follows: B0 open, M2 and ST closed during stimulation.

For a unipolar stimulation configuration, stimulation pulses are delivered between the distal electrode and the housing 40. The voltage of the proximal electrode is floating and the housing 40 is connected to the ground. The switches are configured as follows: B0 closed, M2 open, and ST closed for the duration of the stimulation.

The invention proposes to modify the generator and its control software, adding a link—indicated by a thick line in FIG. 2—between terminal 26 of the generator (connected to the proximal electrode 16) and the metal housing 40 of the generator. According to one embodiment, this connection is selectively closed by actuation of a switch SV for the ventricular stage. If there is an atrial detection/stimulation stage, the same connection is possible, with a corresponding switch SA.

The purpose of the switches SA and SV is to force to the ground potential the conductor of the proximal electrode 16 (atrial or ventricular) during an MRI examination.

The connection to the ground potential of one of the conductors of the lead is an unconventional operation because the generator normally manages only the unipolar or bipolar configurations of stimulation/detection described above.

According to a preferred embodiment, the switches SA and SV are one of the following types: an electronic relay, and a MEMS switch (and the like) that are controlled by logic gates, said logic gates being controlled by the generator software.

When the conditions for switching to a safekeeping mode are met, the generator software controls the switches of the generator, in accordance with the present invention, and connects the proximal atrial and ventricular conductors to the generator housing and to the electrical ground of said housing during an MRI examination.

According to one embodiment, the generator includes a magnetic field detector employing various techniques for magnetic field detection, for example, detection of core saturation by a coil, detection of magnetic field by a field effect transistor, measurement of a voltage collected by a telemetry antenna, to name a few. The detection techniques of an MRI type magnetic field may be combined with other criteria and implemented in a specific algorithm of the generator software.

According to one embodiment, the safekeeping mode is maintained as long as the relevant conditions are met, for example, as long as the device is subject to an MRI type magnetic field.

When the device is in the safekeeping operating mode, the switches are configured as follows: B0 closed, M1 closed, M2 open, T1 open, and SV closed except temporarily during the short duration of the stimulation in another cavity (see below for detail).

In the safekeeping mode, the configurations of stimulation and detection are hybrid configurations, that is intermediate between the classical unipolar and bipolar configurations. Indeed:

the stimulation is located on the distal electrode of the lead, referring to both the potential of the proximal electrode and to the housing connected to the ground;

the signal detection is of the unipolar type, but with a very short dipole insofar as the ground is connected to the proximal electrode.

Preferably, to avoid coupling between the two ventricular and atrial chambers during a ventricular stimulation, the proximal electrode is not grounded (and vice versa).

As the phase of stimulation is very short (typically 1 ms for the electrical stimulation pulse, followed by 14 ms to discharge the output capacitor), the brief absence of shielding in the atrial stage during ventricular pacing (or vice versa) has no significant impact on the temperature rise of the electrodes, which is a physical phenomenon having a time constant that is large relative to the duration of the stimulation phase.

When the device leaves the safekeeping mode after an MRI examination or more particularly after the disappearance of the detected MRI RF magnetic field, the standard configuration of detection/stimulation (as described above) is restored. The end of the MRI examination period alternately can be based on, for example, a predetermined time period corresponding to a time that would be somewhat longer than a suitable time to complete an MRI examination.

It should be understood that the present invention is equally applicable to a generator that is designed to address a larger number of cardiac chambers, as with devices such as devices of "multisite" type used, for example, for ventricular or atrial cardiac resynchronization.

It should be understood, however, that the safekeeping configuration can not only be used for MRI, but also as a protection in a variety of other electromagnetic environments created by medical devices such as electric scalpels, electrical stimulation devices for transcutaneous nerve stimulation (TENS), as well as equipments of everyday life such as anti-theft gates, devices for monitoring electrical items (EAS), and the like. In addition, the safekeeping configuration can be implemented to avoid the consequences of induced voltages on the lead. For one example, the safekeeping mode can be used to reduce the induced voltage that, if not corrected, could adversely affect the pacing stimulation pulse, e.g., by removing or reducing the stimulation pulse. For another example, the safekeeping configuration can be used to avoid a parasitic stimulation that can be triggered by an induced voltage appearing on the lead.

A further embodiment of the present invention is directed to a generator for an active implantable medical device having a lead for one of a cardiac stimulation, a resynchronization and a defibrillation operation, said generator comprising:
    a metal housing having a ground potential;
    an electronic circuit housed in said metal housing having a first generator connection terminal and a second generator connection terminal, wherein the first and second generator connection terminals respectively receive first and second conducting terminals of a lead;
    a plurality of switches, and
    a switch controller controlling the plurality of switches in a first mode of operation in which at least one of the first and second generator connection terminals is connected to said electronic circuit for sensing cardiac activity and delivering stimulation pulses, and a safekeeping mode of operation in which one of the first and second generator connection terminals is connected to the metal housing ground and the other of the first and second generator connection terminals is connected to the electric circuit for sensing cardiac activity and delivering stimulation pulses.

Preferably, the generator further comprises a magnetic field detector, wherein the switch controller places the electronic circuit in the safekeeping mode in response to a detected magnetic field. The detected magnetic field has a corresponding duration and the switch controller temporarily controls the switches to operate in the safekeeping mode for said duration. The generator preferably includes comprising an amplifier and a pulse generator for respectively sensing cardiac activity and delivering stimulation pulses as needed.

In a preferred embodiment the generator has a first mode of operation that is a bipolar sensing mode in which the metal housing is grounded and the first and second generator connection terminals are connected to the amplifier. The generator also has a safekeeping mode of operation that is a unipolar sensing mode in which the metal housing is grounded and the first generator connection terminal is connected to the amplifier for sensing electrical signals from a patient and the second generator connection terminal is connected to the metal housing.

Further, the generator preferably includes a first mode of operation that is a bipolar stimulation mode in which stimulation pulses are delivered between the first electrode and the second generator connection terminals. The first mode may include both the bipolar sensing and the bipolar detection. Similarly, the generator safekeeping mode of operation preferably includes a unipolar stimulation mode in which stimulation pulses are delivered between the one generator connection terminal and the other generator connection terminal. The safekeeping mode may include both the unipolar detection and unipolar stimulation.

One skilled in appreciate that the present invention can be practiced by other than the embodiments described herein, which are presented for purposes of illustration and not of limitation.

The invention claimed is:

1. An implantable medical device comprising:
    a lead comprising a first conductor and a second conductor; and
    a generator comprising an electronic circuit and a metal housing, wherein the electronic circuit is configured to perform at least one of a sensing operation and a stimulation operation, and wherein the metal housing has a ground potential;
    wherein the generator comprises one or more switching devices configured to switch between a normal configuration and a safekeeping configuration, wherein (i) the one or more switching devices, in the safekeeping configuration, are configured to disconnect the second conductor from the electronic circuit and to connect the second conductor to the ground potential of the metal housing, (ii) the first conductor is connected to the electronic circuit in the safekeeping configuration, and (iii) the one or more switching devices, in the safekeeping configuration, are configured to cause the second conductor to shield the first conductor from at least a portion of the effects of the magnetic field while the first conductor remains connected to the electronic circuit for use in performing the at least one of the sensing operation and the stimulation operation.

2. The implantable medical device system of claim 1, wherein the lead is a coaxial lead, wherein the first conductor is an inner conductor and the second conductor is an outer conductor that radially surrounds and is coaxial with the first conductor, and wherein the outer conductor, in the safekeeping configuration, is configured to shield the inner conductor against at least a portion of the effects of the magnetic field.

3. The implantable medical device system of claim 1, wherein the lead is a co-radial lead, wherein the first conductor is a first spiral conductor and the second conductor is a second spiral conductor having a same radius as the first spiral conductor and being positioned to a side of the first spiral conductor within the lead, and wherein the second spiral conductor is configured to shield the first spiral conductor against at least a portion of the effects of the magnetic field.

4. The implantable medical device system of claim 1, wherein the magnetic field is an MRI magnetic field and the one or more switching devices are configured to switch into the safekeeping configuration during an MRI examination.

5. The implantable medical device system of claim 1, wherein the generator further comprises a switch controller for operating said one or more switching devices in one of a first set of positions corresponding to said safekeeping operation and a second set of positions corresponding to the normal configuration, wherein the second conductor is not connected to the ground potential of the metal housing in the normal configuration.

6. The implantable medical device system of claim 5, further comprising a magnetic field detector, wherein said switch controller is responsive to a detected magnetic field to place said one or more switching devices in said first set of positions.

7. The implantable medical device system of claim 6, wherein the lead further comprises a first electrode connected to the first conductor and a second electrode connected to the second conductor, and wherein the electronic circuit further comprises an amplifier for sensing cardiac activity and a pulse generator for delivering stimulation pulses.

8. The implantable medical device system of claim 7, wherein the generator operates in a bipolar sensing mode, and wherein the second set of positions connects the first and second electrodes to the amplifier and not the metal housing ground.

9. The implantable medical device system of claim 8, wherein the generator operates in a unipolar sensing mode, and wherein the first set of positions connects the first electrode to the amplifier and the second electrode to the metal housing ground.

10. The implantable medical device system of claim 7, wherein the generator operates in a bipolar stimulation mode, wherein the second set of positions connects the first and second electrodes to the pulse generator and not the metal housing ground, and wherein stimulation pulses are delivered between the first and the second electrodes.

11. The implantable medical device system of claim 10, wherein the generator operates in a unipolar stimulation mode, wherein the first set of positions connects the first electrode to the pulse generator and the second electrode to the metal housing ground, and wherein stimulation pulses are delivered between the first electrode and the metal housing ground.

12. A generator for an implantable medical device, the generator comprising:
a metal housing having a ground potential;
an electronic circuit housed in said metal housing having a first generator connection terminal and a second generator connection terminal, wherein the first and second generator connection terminals are configured to be respectively electrically coupled to a first conductor of a lead and a second conductor of the lead;
one or more switching devices, and
a switch controller configured to control a configuration of the one or more switching devices, wherein, in a first mode of operation, the switch controller is configured to cause the one or more switching devices to connect at least one of the first and second generator connection terminals to the electronic circuit for performing at least one of a sensing operation and a stimulation operation, wherein, in a safekeeping mode of operation, the switch controller is configured to cause the one or more switching devices to connect the second generator connection terminal to the metal housing and the first generator connection terminal to the electric circuit for performing the at least one of the sensing operation and the stimulation operation, and wherein, in the safekeeping mode, the switch controller is configured to cause the second conductor to shield the first conductor from at least a portion of effects of a magnetic field while the first conductor is used for performing the at least one of the sensing operation and the stimulation operation.

13. The generator of claim 12, further comprising a magnetic field detector, wherein the switch controller places the plurality of switches in the safekeeping mode in response to a detected magnetic field.

14. The generator of claim 13, wherein the detected magnetic field has a corresponding duration, and wherein the switch controller temporarily controls the switches to operate in the safekeeping mode for the duration.

15. The generator of claim 14, further comprising an amplifier and a pulse generator.

16. The generator of claim 15, wherein the first mode of operation is a bipolar sensing mode in which the metal housing is grounded and the first and second generator connection terminals are connected to the amplifier.

17. The generator of claim 16, wherein the safekeeping mode of operation is a unipolar sensing mode in which the metal housing is grounded, the first generator connection terminal is connected to the amplifier for sensing electrical signals from a patient, and the second generator connection terminal is connected to the metal housing.

18. The generator of claim 15, wherein the first mode of operation is a bipolar stimulation mode in which stimulation pulses are delivered between the first electrode and the second generator connection terminals.

19. The generator of claim 18, wherein the safekeeping mode of operation is a unipolar stimulation mode in which stimulation pulses are delivered using only the first conductor.

* * * * *